US00PP35026P2

(12) United States Plant Patent
Wheeler et al.

(10) Patent No.: US PP35,026 P2
(45) Date of Patent: Mar. 14, 2023

(54) BLUEBERRY PLANT NAMED 'BB14-232PT-2'

(50) Latin Name: *Vaccinium corymbosum*
Varietal Denomination: BB14-232PT-2

(71) Applicant: BB IP Repository, LLC, Grand Junction, MI (US)

(72) Inventors: Edmund J. Wheeler, Holland, MI (US); Maria Pilar Banados, Santiago (CL)

(73) Assignee: BB IP Repository, LLC, Grand Junction, MI (US)

( * ) Notice: Subject to any disclaimer, the term of this patent is extended or adjusted under 35 U.S.C. 154(b) by 0 days.

(21) Appl. No.: 17/714,364

(22) Filed: Apr. 6, 2022

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 6/368; A01H 5/368
See application file for complete search history.

*Primary Examiner* — Anne Marie Grunberg
(74) *Attorney, Agent, or Firm* — King IP Law; Joshua King

(57) ABSTRACT

'BB14-232PT-2', is the second known genotype selected in a tropical environment of Peru. 'BB14-232PT-2' does not require chill-hours for either budbreak or fruit production, possibly because 'BB14-232PT-2' does not develop endo-dormancy. The fruit of 'BB14-232PT-2' is a medium to large size berry, with medium dark blue color, excellent fruit firmness and crunchy texture. The eating quality of 'BB14-232PT-2' is excellent and superior to many of the varieties currently grown in Peru, with a sugar/acidity balance of 16 to 20. Time of fruit production in 'BB14-232PT-2' can be regulated by the pruning date and environment conditions.

13 Drawing Sheets

Latin name: *Vaccinium corymbosum.*
Common name: Blueberry.
Cultivar name: 'BB14-232PT-2'.

BACKGROUND AND SUMMARY

Blueberries are a well-known fruit enjoyed by many throughout the world. The novel blueberry variety in this application, 'BB14-232PT-2', is the second genotype selected in the tropical environment of Peru.

One example of an existing known blueberry variety in the same environment is 'Ventura', U.S. Plant Pat. No. 24,606. Compared to 'Ventura', 'BB14-232PT-2' has lower vigor and smaller plant size. The fruit of 'BB14-232PT-2' is located on the apical portion of vertical shoots, is well presented on the plant and is produced in current season shoots rather than in 1-year-old shoots, The fruit of 'BB14-232PT-2' is firm, has sweet flavor and medium to large size. 'BB14-232PT-2' has firm berries and a good balance of sweetness and acidity.

Comparing 'BB14-232PT-2' to 'Stellar' (brand name for "BB06-50FL-1", U.S. Plant Pat. No. 30,445), the fruit of 'BB14-232PT-2' is smaller in size, has a darker blue color, has less persistent bloom (wax that covers the fruit) and a flatter shape. The fruiting wood of 'BB14-232PT-2' has a yellow green color compared to olive green for 'Stellar'.

Additional examples of an existing, patented blueberry variety include 'Rocio', U.S. Plant Pat. No. 20,374, and 'Emerald', U.S. Plant Pat. No. 12,165. 'BB14-232PT-2' has lower acidity than these two varieties, shown in Table 1, which Table also provides fruit characteristics of 'BB14-232PT-2' compared to several other commercial varieties grown in Peru.

TABLE 1

Fruit characteristics of several blueberry varieties grown in Chao, Peru compared to BB12-232PT-2. Data is based on the average of several samples of fruit taken during harvest season 2019-2020.

| Cultivar | Fruit size (g) | Firmness Baxlo (shore) | Sugar Content (°brix) | Acidity (%) | Ratio °Brix/ Acidity |
|---|---|---|---|---|---|
| Ventura | 2.3 | 78 | 11.9 | 1.15 | 10.3 |
| Rocio | 3.2 | 76 | 11.5 | 0.90 | 12.7 |
| Stellar | 5.3 | 75 | 12.0 | 0.72 | 16.6 |
| Emerald | 2.1 | 75 | 10.1 | 1.20 | 8.4 |
| BB14-232PT-2 | 3.1 | 78 | 13.0 | 0.81 | 16.0 |

The present cultivar, 'BB14-232PT-2', provides one or more advantages compared to these and/or other blueberry varieties.

The fruit of 'BB14-232PT-2' is medium dark blue color, with excellent firmness and crunchy texture. The eating quality of 'BB14-232PT-2' is very good, having a sugar/acidity balance of 12 to 20, higher than other commercial cultivars in Peru such as Ventura, Rocio or Emerald. 'BB14-232PT-2' is a highly productive variety with very early maturity fruit and very good fresh market quality and storage ability. Time of fruit production in 'BB14-232PT-2' can be regulated by the pruning date and moderated by environmental conditions, and is another distinct characteristic of 'BB14-232PT-2', particularly in this new tropical environment (Peru, for example) for blueberries. 'BB14-232PT-2' does not require chill-hours for either budbreak or fruit production, which may be because 'BB14-232PT-2' does not develop endo-dormancy. 'BB14-232PT-2' was selected in sandy soil in Chao, Peru and tested also under substrate soilless production.

Areas of adaptation of 'BB14-232PT-2' include coast of Peru, Ecuador, and Colombia and other tropical areas with no chill conditions. 'BB14-232PT-2' is under trial in the temperate area of Chile.

Plants of 'BB14-232PT-2' are medium upright with a medium size crown. 'BB14-232PT-2' produces many upright canes, with good leafing and flowering.

The fruit of 'BB14-232PT-2' is moderate sweet with medium acid, and have a firm and crunchy berry adapted to a tropical non-chill environment. The berry scar of 'BB14-232PT-2' is small and dry. 'BB14-232PT-2' shows long fruit storability of about 4 to 5 weeks. The productivity of 'BB14-232PT-2' is higher than 'Kestrel' (U.S. Plant Pat. No. 21,719) and similar 'Rocio' in Peru, although 'BB14-232PT-2' has yet not been tested commercially.

The flowering period of 'BB14-232PT-2' is similar to 'Rocio' in the same tropical environment of Peru. Flowering of 'BB14-232PT-2' starts 55 to 60 days after pruning, which is shorter than 'Scintilla' (U.S. Plant Pat. No. 19,233) and 'Ventura', which take about 120 to 150 days. The fruiting period of 'BB14-232PT-2' is similar to 'Kestrel' and 'Rocio', starting about 130 to 140 days after pruning and lasting for 6 to 7 months. Ripening of 'BB14-232PT-2' is extended and 'BB14-232PT-2' is presented in two flushes of harvest and keeps a uniform berry size during the season.

BRIEF DESCRIPTION OF THE PHOTOGRAPHS

FIG. 3A shows unripe fruit, FIG. 3B shows fruit with wax, FIG. 3C shows fruit with wax removed and a color identification card, and FIG. 3D shows fruit in a clamshell.

DETAILED DESCRIPTION

Figure 1A:
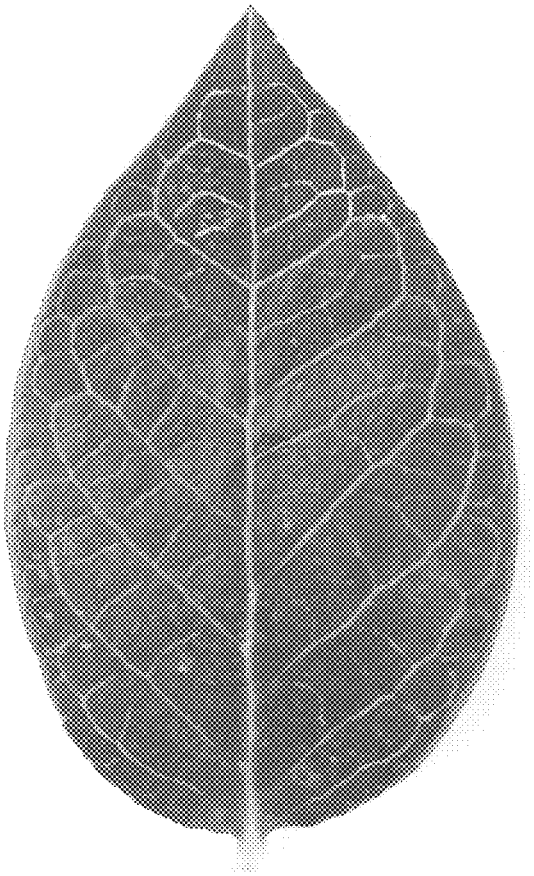
FIGS. 1A and 1B are close-up photographs of 'BB12-232PT-2' taken in Sept 2021, Chao, Peru, and showing the mature leaf color, shape, venation, and petioles. 1B. Shows the young leaf color.
Figure 1B:
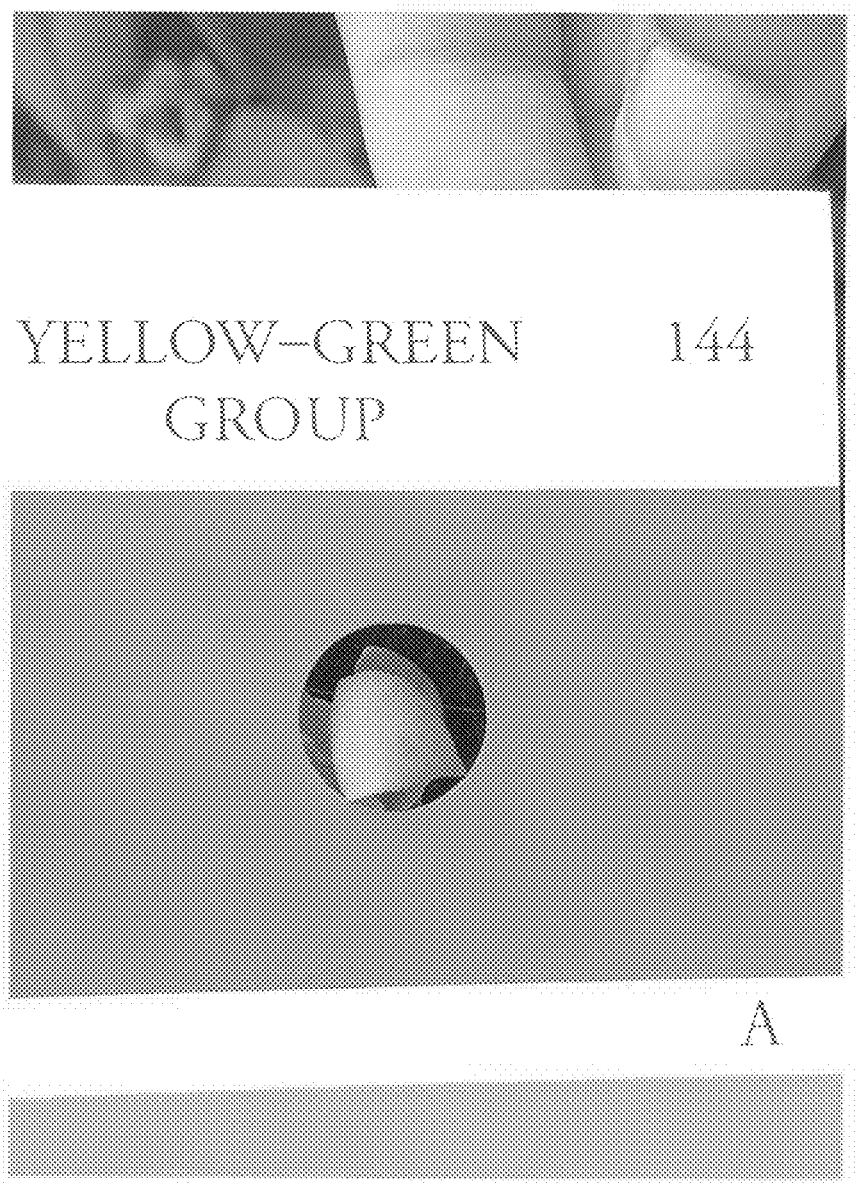
Figure 2A:
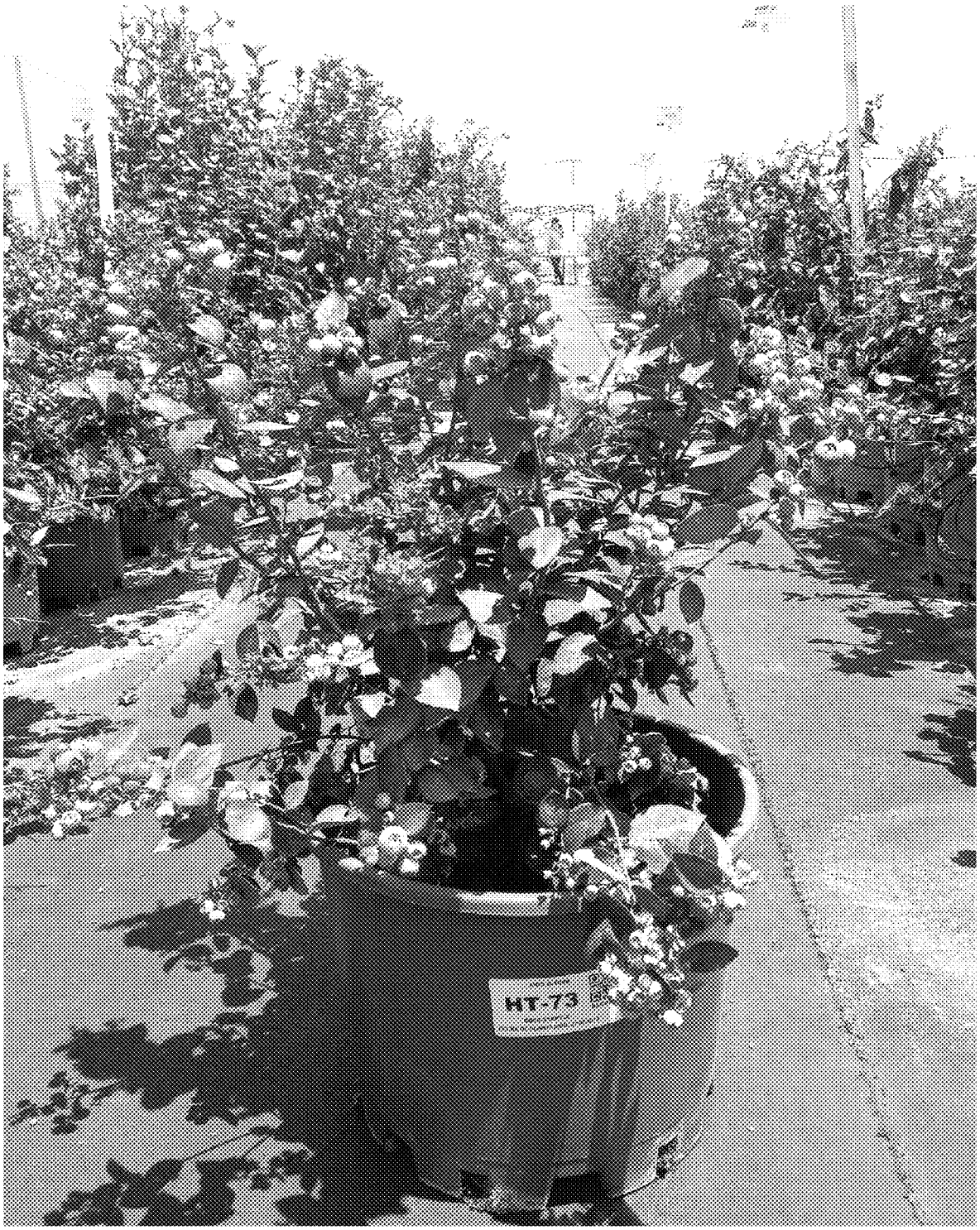
FIGS. 2A and 2B are close-up photographs taken in October 2021, in Chao, Peru, showing one of the clonal 2-years-old plants (2A) growing in containers and the color and shape of mature canes of 'BB14-232PT-2'.
Figure 2B:
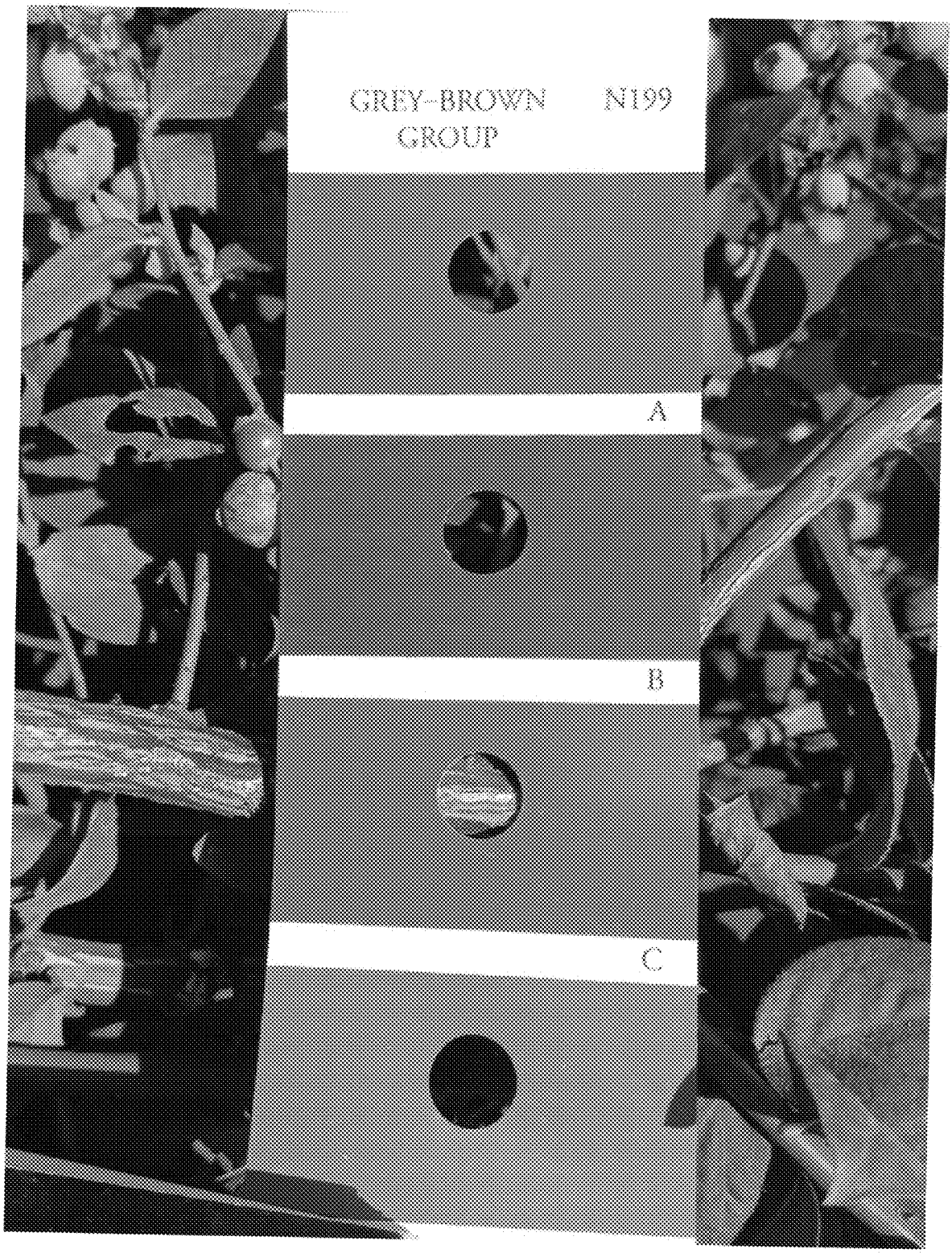
Figure 3A:
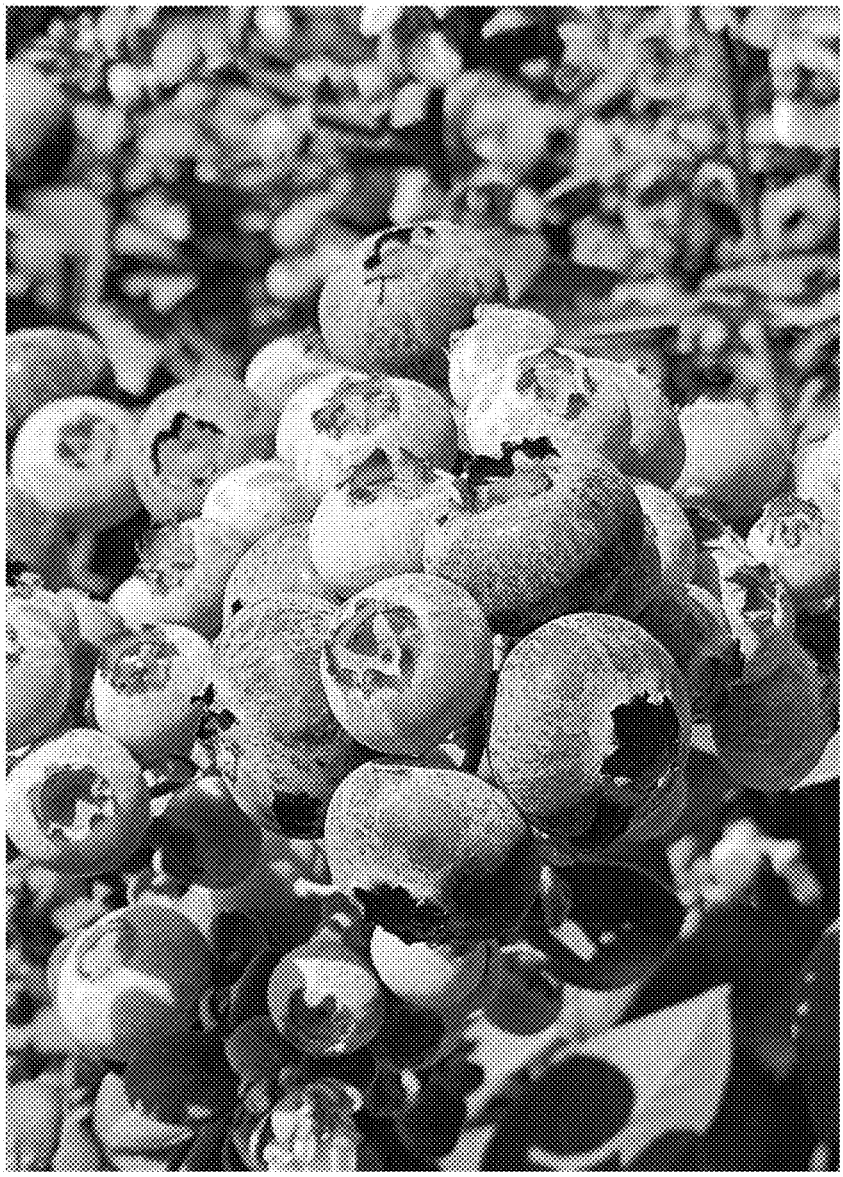
FIGS. 3A, 3B, 3C and 3D are photographs of 'BB14-232PT-2' fruits in different stage of maturity.
Figure 3B:
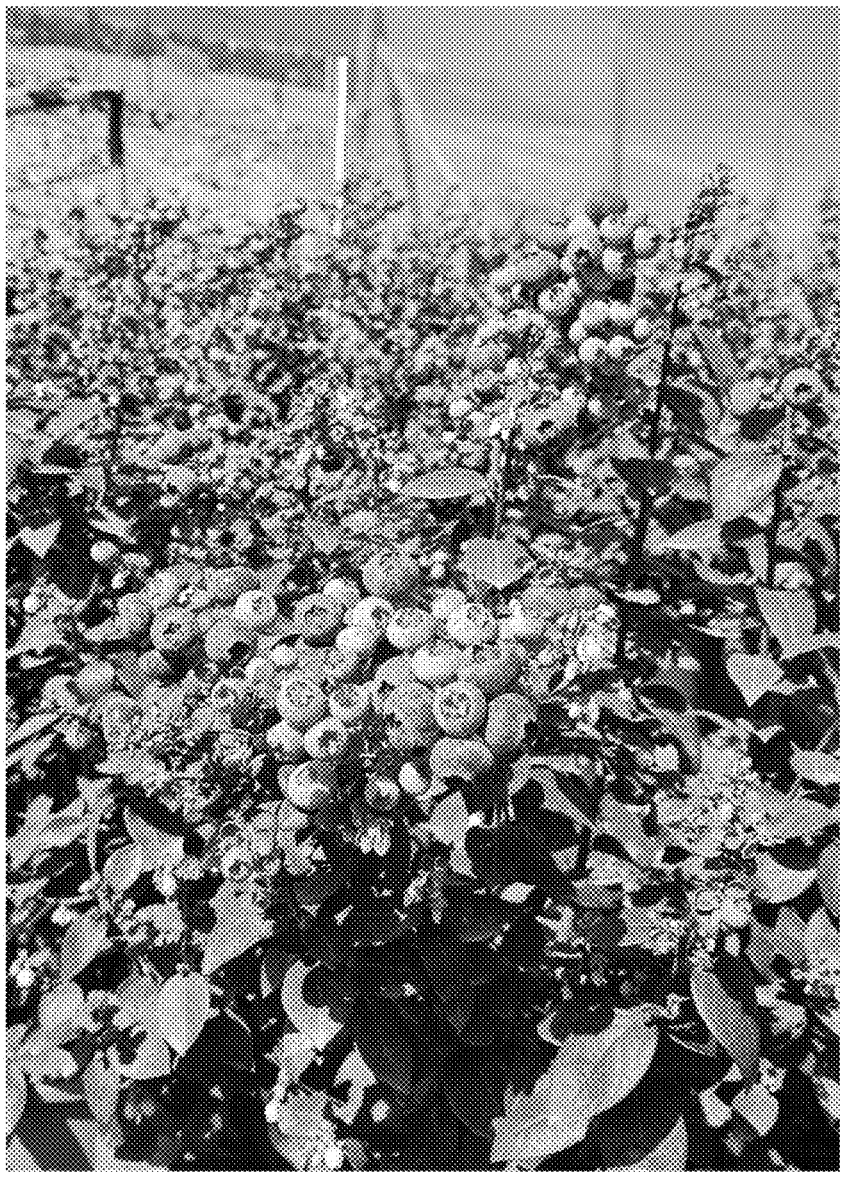
Figure 3C:
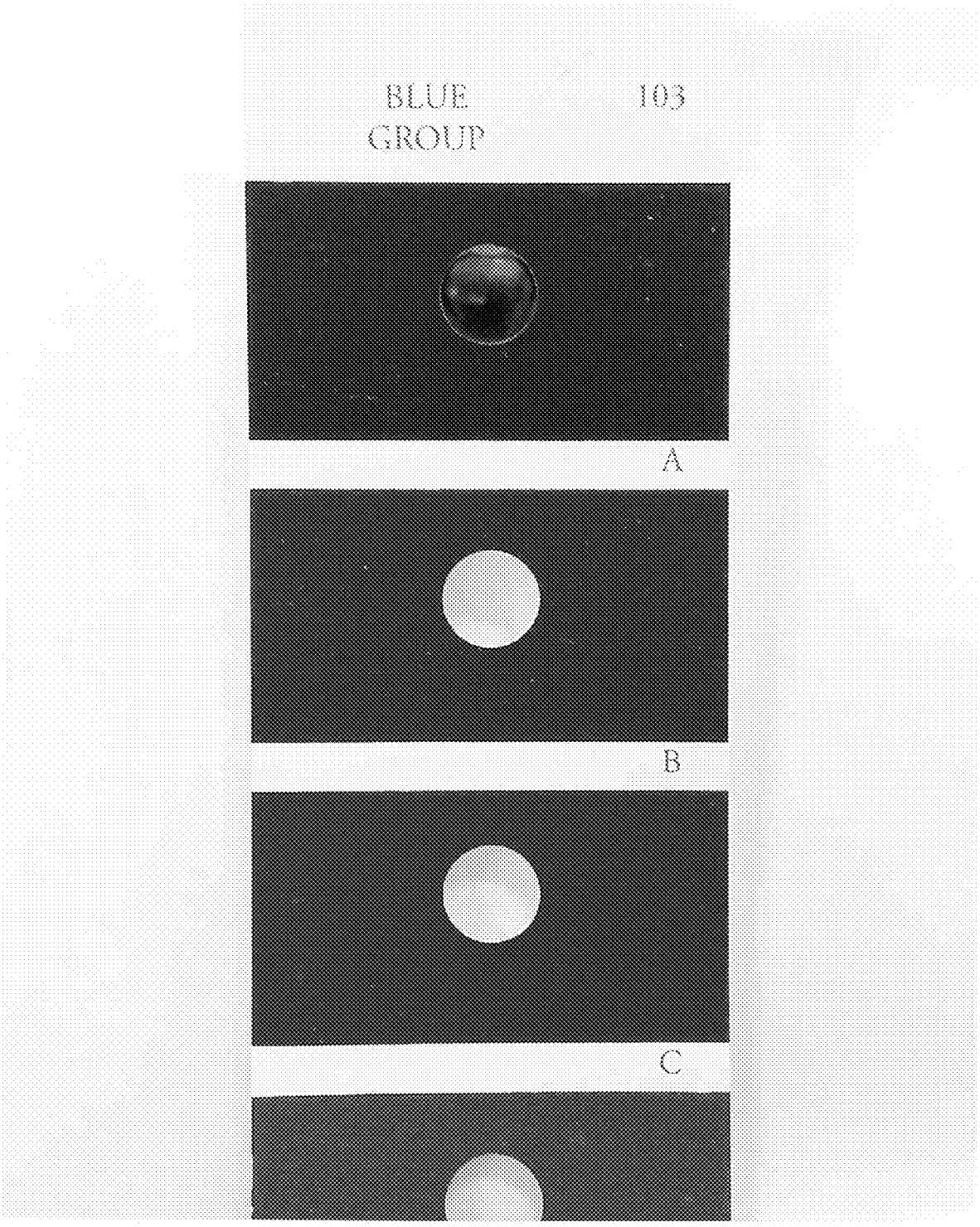
Figure 3D:
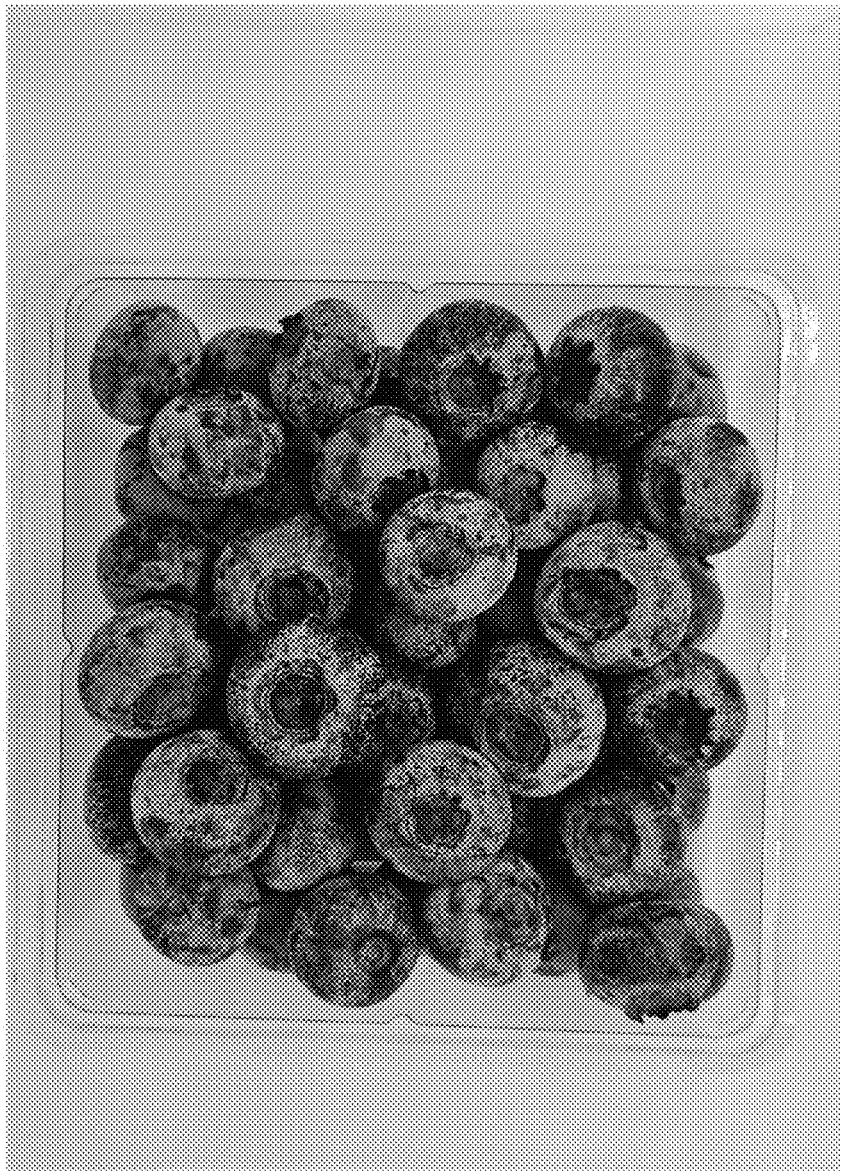
Figure 4A:
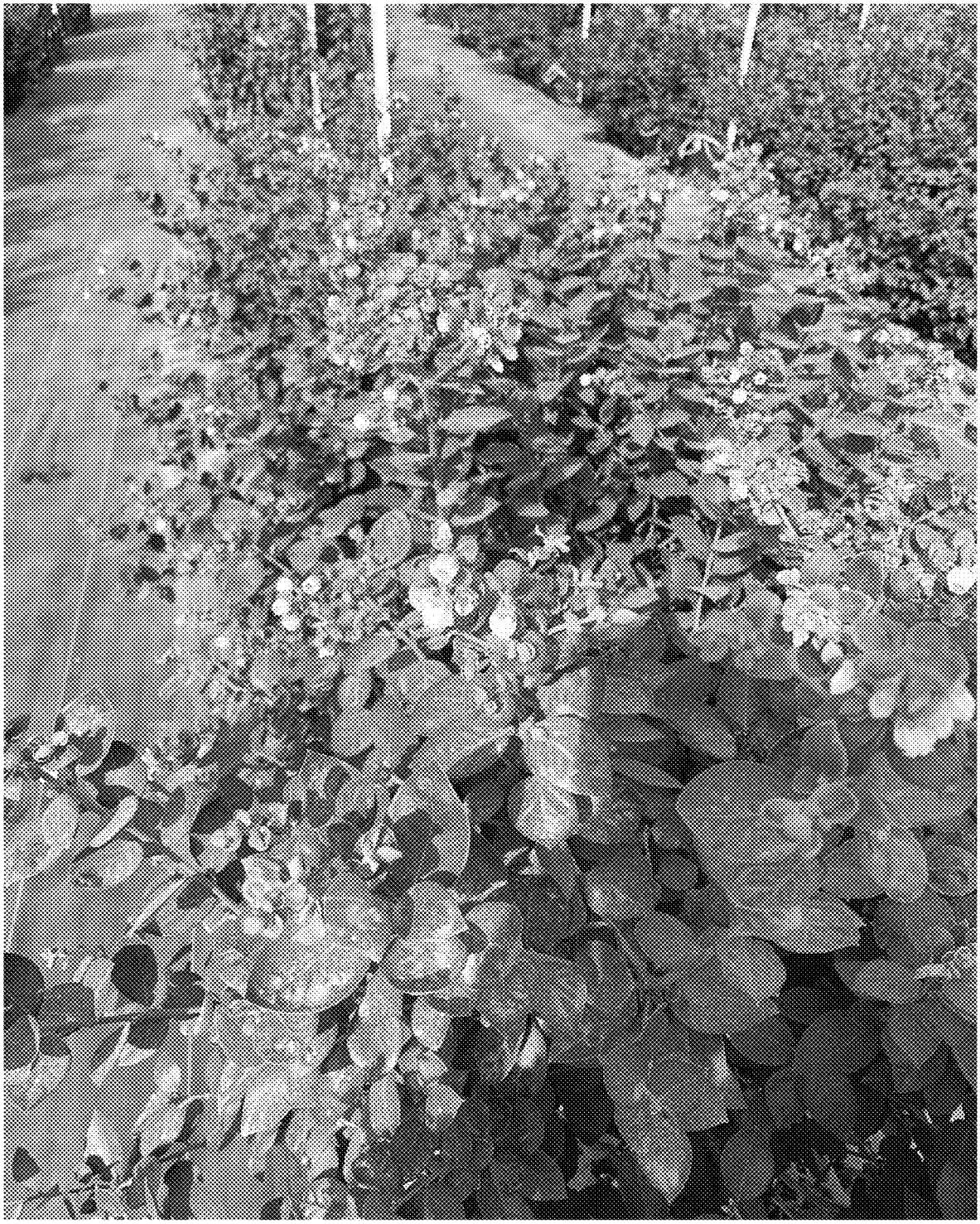
FIGS. 4A, 4B and 4C are close-up photographs of 'BB14-232PT-2' taken in March, 2022 (FIG. 4A) or October 2021, in Chao, Peru, showing the size, shape, and color of a flower and stamen length.
Figure 4B:
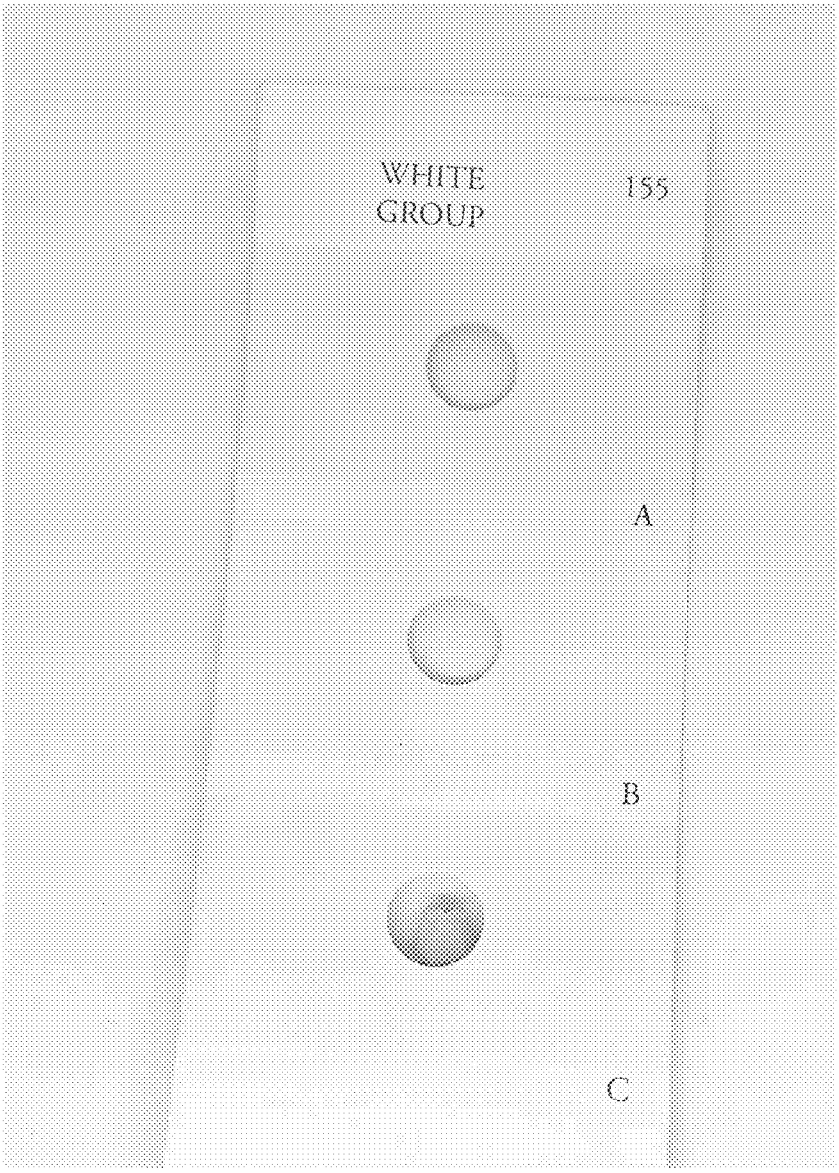
Figure 4C:
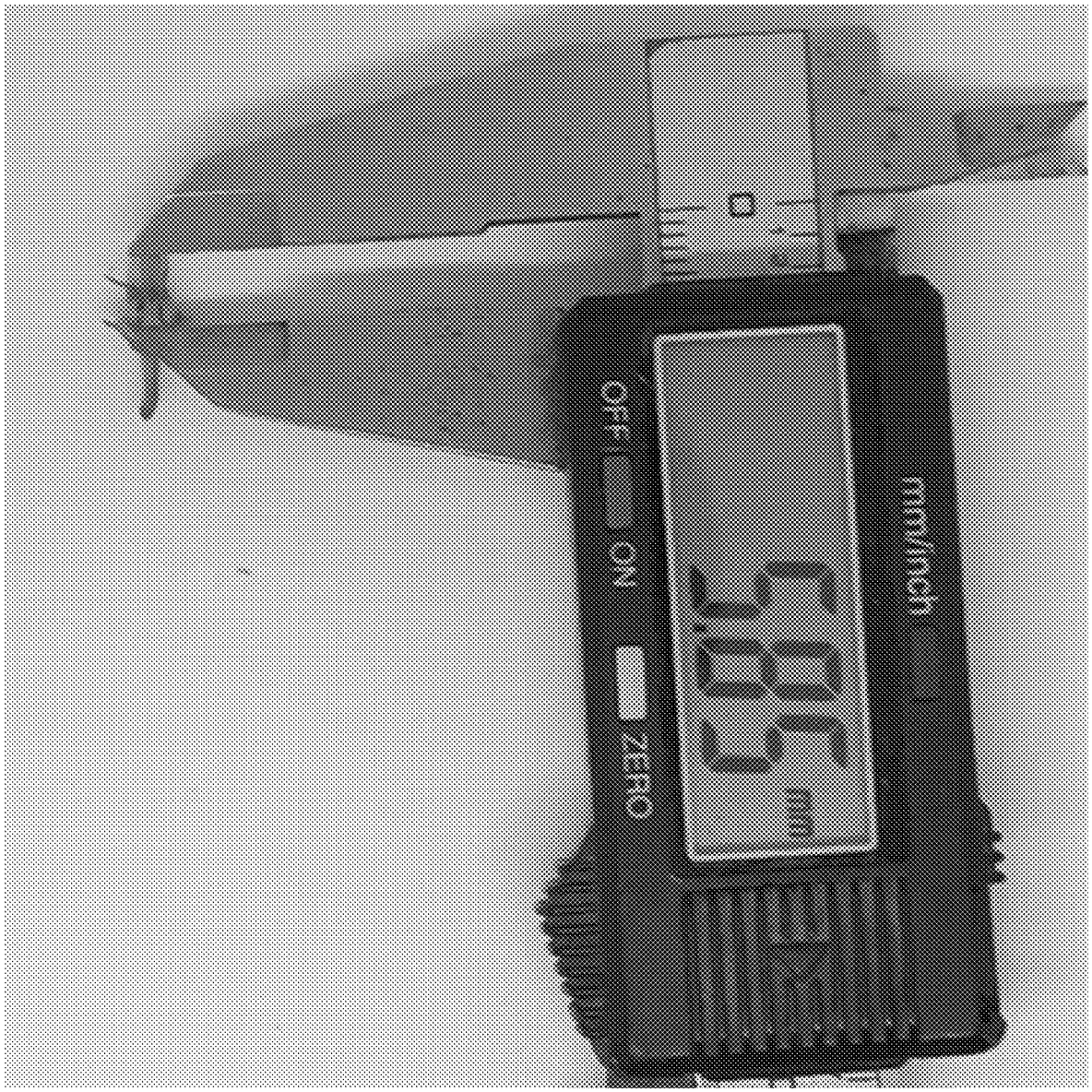
Figure 5A:
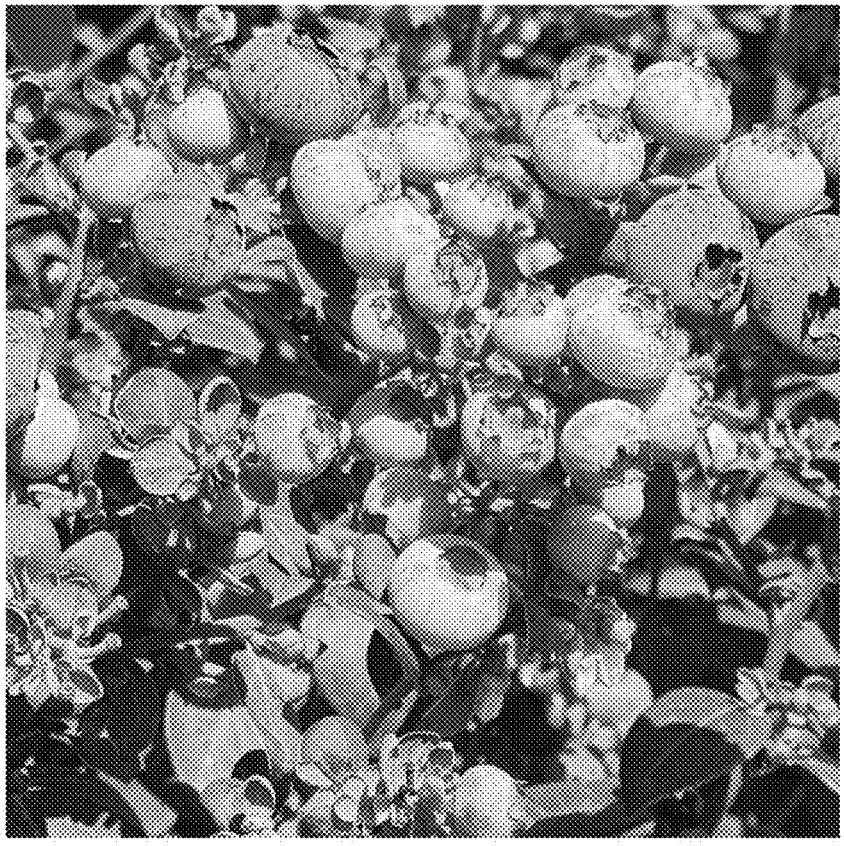
FIGS. 5A and 5B are close-up photographs of 'BB14-232PT-2' taken in October 2021, Chao, Peru, and show the plant with fruiting laterals and fruiting clusters.
Figure 5B:
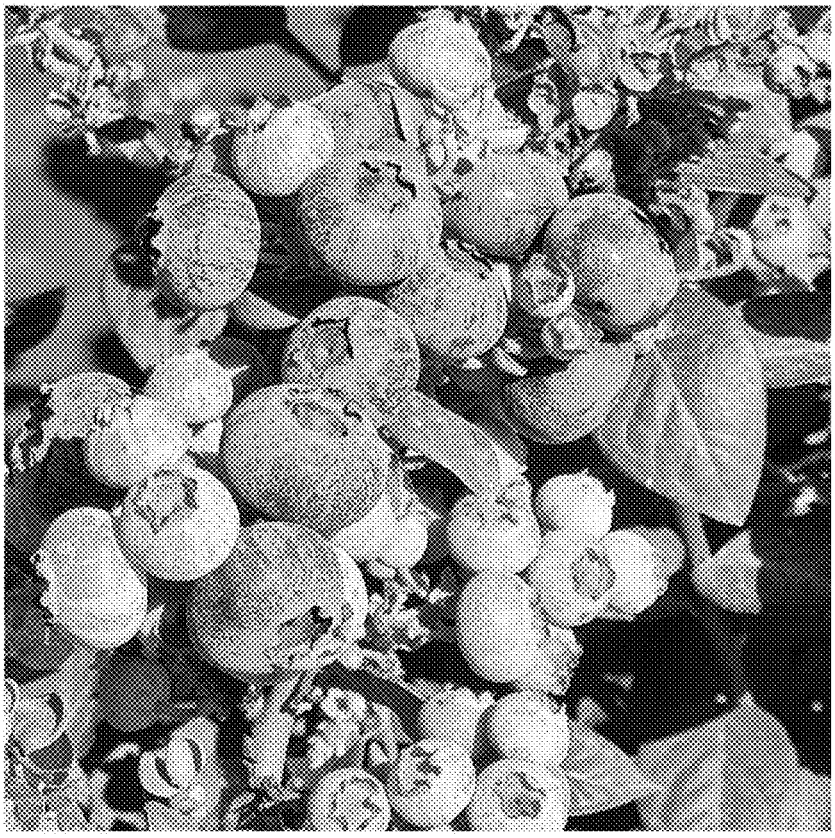

Note: statements of characteristics herein represent exemplary observations of the cultivar performance in Chao, Peru 8° 35'12"S 78° 35'58"W and will vary depending on time of year, location, annual temperature conditions and weather, etc. Where dimensions, sizes, colors, and other characteristics are given, it is to be understood that such characteristics are approximations and averages. The descriptions reported herein are based on the original selected individual bush observed in successive years through 2017, 2018, 2019, 2020 and 2021 in fields near Chao, Peru and also in cloned plants planted in Chao, Peru in 2019 and 2020. Laboratory analysis of fruit characteristics were done in Chao, Peru.

Cultivar name: 'BB14-232PT-2'.

Classification:

Family: Ericaceae.

Botanical name: *Vaccinium corymbosum.*

Common name: Blueberry.

Parentage:

FEMALE PARENT

Name: 'Emerald' (child of, FL91 69 (unpatented) x NC1528 (unpatented)).

U.S. plant patent: U.S. Plant Pat. No. 12,165

Compared to 'Emerald', 'BB14-232PT-2' is sweeter and less acidic, has larger fruit size and firmer berries in the same environment of Chao, Peru.

MALE PARENT

Name: 'BB06-538MX-2' (child of 'Sapphire' (U.S. Plant Pat. No. 11,829) and 'Palmetto' (U.S. Plant Pat. No. 16,756).

U.S. Plant Patent: Unpatented.

Compared to 'BB06-538MX-2', the fruit of 'BB14-232PT-2' is larger, firmer, and less aromatic. They both produce fruit on current season shoots.

'BB14-232PT-2' originated as a seedling selected from a cross of 'Emerald' and 'BB06-538MX-2' made in a greenhouse in Grand Junction, Mich. in 2014. Seed was germinated in Chile and plants of that cross were grown and then sent and planted in a seedling evaluation site in Chao, Province of La Libertad, Peru in February 2016. The plant was first selected in August 2016 based on its excellent fruit characteristics both in the field and after 5 days cold storage and was given the number 'BB14-232PT-2'. 'BB14-232PT-2' was tested under this number for three years. The individual bush was observed and evaluated for productivity and fruit quality in the same site for three successive years from 2016 through 2018. An additional 40 bushes were propagated in vitro and planted in an advanced trial both in soil and in a soilless system near Chao, Peru in July 2019, and the fruit was evaluated in 2020 and 2021. All the observed bushes have retained the characteristics of the original selection.

'BB14-232PT-2' has been asexually propagated via tissue-cultured micro shoots since 2018. Propagated plants have been under evaluation in Chao, Peru since July 2019.

General description of 'BB14-232PT-2'.

'BB14-232PT-2' is a new and distinct non-chill tetraploid Southern/Tropical highbush blueberry variety (*Vaccinium*) of complex ancestry, based largely on *V. corymbosum* and *V. darrowii*, from the breeding program of BBIP. 'BB14-232PT-2' is a very productive early-season variety of short cycle from pruning to harvest, with high quality fresh market characteristics 'BB14-232PT-2' is particularly well suited to be cultivated in tropical areas. 'BB14-232PT-2' has a semi-upright bush and a medium sized crown with many new vertical canes. The bush has a medium vigor and is very productive. 'BB14-232PT-2' has shown very good adaptability to sandy soil and substrate mix of coco fiber and peat. The fruit itself is medium dark blue color, with high firmness and crunchy texture. The eating quality is excellent with a higher sugar/acidity balance than 'Emerald', 'Ventura' or 'Rocio' in Peru. Fruit should be picked on a regular schedule of about 7 to 9 days to maintain the quality of the fruit. 'BB14-232PT-2' will be released as a second cultivar selected in Peru and it is an improvement over 'Emerald', 'Rocio' and 'Ventura' in terms of flavor and overall eating experience.

References to color refer to The Royal Horticultural Society Colour Chart 2007 Fifth Edition.

Morphological characteristics reference: Plant Systematics, Jones and Luchsinger, 2 Ed., McGraw Hill, New York, ISBN 0-07-032796-3, 1986.

Device used to measure Soluble Solids (SS-Brix°), Titratable acidity (TA), pH: PAL-BX/Acid 7, Atago USA, Inc., Bellevue, Wash.

Firmness readings: Shore by BAXLO Durometer (Chao, Peru).

General Description: medium upright with a medium size crown and medium vigor; sweet, medium acid, firm and crunchy berry adapted to a tropical non-chill environment 'BB14-232PT-2' blooms about 55 to 65 days after pruning. The average 50% ripening date is 200 days after pruning. Firmness ranges from 70 to 84 Baxlo Shore, Brix° from 12 to 14% and titratable acidity from 0.7 to 0.95% and sugar to acid ratio of 12 to 20. Storability is long and 'BB14-232PT-2' could last up to 30 days or more in cold storage.

Specific features of the variety:

Plant:

*Growth habit.*—Semi-upright.
*Plant width.*—76 cm at mid-bush height.
*Plant height.*—70 cm.
*Productivity.*—2.1 to 2.7 kg per plant.
*Cold hardiness/tolerance.*—Not tested.
*Chilling requirement.*—This is a tropical highbush and this plant does not require chill hours for bud break.
*Canes.*—Moderately branched, average 5 to 6 shoots per bush, average 60-75 cm length, medium number of laterals.
*Young current-season-shoots.*—Yellow-Green Group 144A.
*One-year-old shoot branches color.*—Yellow-Green Group 144C. Texture is soft. Mature cane color: Pantone Grey Brown N199-C.
*Mature cane texture.*—Rough.
*Fruiting wood.*—Current season shoots. Internode length range: 3 to 4 cm.
*Surface texture of new wood.*—Smooth.
*Time of beginning of leaf bud burst.*—Bud break occurs 8 to 10 days after pruning in Chao, Peru.
*Time of beginning of flowering.*—55 to 60 days after planting or pruning in Chao, Peru.
*Date of 50% open flowers.*—75 to 80 days after planting or pruning in Chao, Peru for the first flush of flowers.
*Time of beginning of fruit ripening.*—Fruit ripening begins on 120 to 140 days after planting or pruning.
*Disease resistance/susceptibility.*—None claimed.
*Young current-season-shoots.*—Yellow green 146-B.
*One-year-old short branches color.*—Yellow green 146-B.

Foliage:

*Young, newly expanded leaf color.*—Upper surface: Yellow green 144-A. Lower surface: Yellow green 145-B.
*Leaf arrangement.*—Simple Alternate.
*Mature, fully expanded leaves.*—Upper surface: Yellow green 147-A. Lower surface: Yellow green 148-C.
*Leaf margins.*—Entire.
*Leaf venation.*—Pinnate.
*Leaf shape.*—Ovate.
*Leaf length.*—56 to 59 mm, average 57 mm.
*Leaf width.*—32 to 35 mm, average 34 mm.
*Leaf color.*—Yellow green 147-A.
*Leaf apices.*—Acuminate. Leaf bases: Acute.
*Vein and petiole coloration.*—Color vein: Yellow green 144-D. Color petiole: Yellow green 145-B.
*Petiole length.*—3 mm.
*Petiole diameter.*—2 mm.
*Evergreen.*—This variety is evergreen and keep its leaves during the entire year Fall leaf color: Does not apply for this genotype since it keeps the leaves year round.

Leaf dimensions:

*Overall shape.*—Ovate.
*Length.*—56 to 59 mm, average 57 mm.
*Width.*—32 to 35 mm, average 34 mm.
*Leaf margins.*—Entire, no visible (microscope 10×) pubescence and a few nectaries.
*Leaf surface.*—Smooth upper and lower, no visible (microscope 10×) pubescence.

Leaf buds:

*Shape.*—Medium obtuse.
*Length.*—2.5 mm.
*Width.*—2 mm.
*Color.*—Greyed-orange 175-A.

Flower buds:

*Shape.*—Round.
*Length.*—4 mm.
*Width.*—3.5 mm.
*Color.*—Greyed-orange 175-A.

Flower:

*Flower shape.*—Globose.
*Number per lateral.*—5 to 8.
*Flowers per cluster.*—7 to 10.
*Flower fragrance.*—Light floral.
*Corolla color.*—White 155-C.
*Corolla length.*—7.17 mm.
*Corolla width.*—8.08 mm.
*Corolla aperture width.*—4.4 mm.
*Corolla texture.*—Smooth.
*Flower peduncle length.*—6.5 mm.
*Peduncle diameter.*—1.4 mm.
*Peduncle texture.*—Smooth.
*Peduncle color.*—Yellow green 144-C.
*Flower pedicel length.*—5.42 mm.
*Pedicel diameter.*—1.12 mm.
*Pedicel texture.*—Smooth.
*Pedicel color.*—Yellow Green 144-D.
*Calyx (with sepals).*—3.14 mm.
*Calyx color.*—Yellow-Green 147-B,C.
*Fruit attitude of the sepals.*—Incurved.
*Stamen length.*—5 to 6 mm.
*Stamen number per flower.*—10.
*Stamen filament color.*—Greyed-green 193-B.
*Style.*—8.3 mm, top of ovary to stigma tip.
*Style color.*—Yellow-Green 145-B.
*Pistil extends over the top of corolla.*—1 mm.
*Ovary color.*—Yellow Green 147-B.
*Anther length.*—4.36 mm.
*Number.*—1.
*Anther color.*—Greyed-orange N167-A.

Pollen:

*Abundance.*—Medium high.
*Color.*—Yellow 8-D.

Fruit:

*Date of 50% maturity.*—200 to 230 days after pruning.
*Duration of ripening.*—Average 65 to 80 days from bloom to ripen in Olmos, Peru and Chao, Peru. Ripening period can last 6 months.

*Yield.*—3 kg per plant.
*Cluster density*.—Medium.
*Immature fruit color*.—Green 130-D.
*Berry color with wax.*—Violet Blue 95-D.
*Berry color with wax removed*.—Blue 103-A.
*Berry flesh color*.—Green 142-C.
*Berry surface wax abundance*.—Moderately persistent.
*Berry weight*.—Average 2.7 to 3.3 grams/berry.
*Berry size diameter.*—19.6 mm.
*Berry height.*—13.7 mm.
*Berry width.*—19.6 mm.
*Aspect* (*h/w*).—0.70.
*Berry shape*.—Oblate.
*Average number of fruits per cluster.*—5 to 8.
*Detachment force*.—Easy.
*Self-fruitfulness*.—Fair, cross pollination may be desirable for maximum yield and fruit size Fruit stem scar: 1.2 mm diameter, 1 mm depth.
*Calyx.*—5 lobed with pronounced ridges.
*Calyx diameter.*—10.9 mm.
*Calyx depth.*—1 mm.
*Berry firmness*.—Firm, 75 to 80 Shore of Baxlo.
*Berry sweetness*.—High, Brix°=12 to 14.
*Berry acidity*.—Titratable acidity=0.7% to 0.95%.
*Berry flavor and texture*.—Good blueberry flavor, balanced sugar and acidity, and crunchy texture.
*Storage ability*.—Medium high, 3-4 weeks in refrigerated storage.
*Suitability for mechanical harvesting*.—Not tested.

Seed:

*Seed abundance in fruit*.—Medium, 12-17 seed per fruit Seed color: Pantone Greyed-orange group 177A.
*Seed dry weight.*—9 mg.
*Seed size.*—0.5 mm length, 0.5 mm width.

Possible typical market uses: Mainly fresh market. 'BB14-232PT-2' can also be used for processing and/or as frozen fruit.

What is claimed is:

1. A new tropical highbush blueberry plant cultivar named 'BB14-232PT-2' as described and shown herein.

* * * * *